United States Patent

Kristiansson et al.

[19]

[11] Patent Number: 6,139,796
[45] Date of Patent: *Oct. 31, 2000

[54] METHOD FOR STERILIZING FLOWABLE PRODUCT PACKAGES

[75] Inventors: Anders Kristiansson; Martin Eliasson, both of Lund; Lars Näslund, Furulund, all of Sweden

[73] Assignee: Tetra Laval Holdings & Finance, Pully, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 09/011,289
[22] PCT Filed: Jul. 9, 1996
[86] PCT No.: PCT/SE96/00928
 § 371 Date: Apr. 13, 1998
 § 102(e) Date: Apr. 13, 1998
[87] PCT Pub. No.: WO97/07024
 PCT Pub. Date: Feb. 27, 1997

[30] Foreign Application Priority Data

Aug. 11, 1995 [SE] Sweden ................................. 9502812

[51] Int. Cl.[7] ...................................................... A46L 2/08
[52] U.S. Cl. .............................. 422/22; 422/302; 53/425; 250/492.3
[58] Field of Search ................................. 422/4, 22, 23, 422/120, 121, 186, 186.05, 186.16, 186.18, 302, 304, 305, 906; 250/396 R, 427, 432, 492.3; 53/425

[56] References Cited

U.S. PATENT DOCUMENTS

| | | | |
|---|---|---|---|
| 2,602,751 | 7/1952 | Robinson | 422/22 |
| 3,780,308 | 12/1973 | Nablo | 250/492.3 |
| 3,942,017 | 3/1976 | Uehara et al. | 250/492.3 |
| 4,652,763 | 3/1987 | Nablo | 250/492.3 |
| 5,011,660 | 4/1991 | Arena | 422/23 |
| 5,422,068 | 6/1995 | Shalaby et al. | 422/33 |
| 5,489,783 | 2/1996 | Kristiansson | 250/492.3 |
| 5,512,244 | 4/1996 | Griffiths et al. | 422/33 |
| 5,730,933 | 3/1998 | Peterson | 422/22 |

OTHER PUBLICATIONS

Rangwall et al., 'Electron-beam sterilization and its application to aseptic packaging', Pharmaceutical Technology, 36-47, Nov. 1985.

*Primary Examiner*—Robert J. Warden, Sr.
*Assistant Examiner*—Theresa T. Snider
*Attorney, Agent, or Firm*—James Ray & Associates

[57] ABSTRACT

A method for sterilizing the inside of a container which is ready to be filled, or a package material for a container in the form of a sheet or web wherein such sterilization is effected by way of radiation with an electron beam in combination with a gas stream contacting the beam, while the electron gun and container or package material are in relative motion towards each other.

15 Claims, 2 Drawing Sheets

METHOD FOR STERILIZING FLOWABLE PRODUCT PACKAGES

FIELD OF THE INVENTION

The present invention relates to a method for sterilizing a container which is ready to be filled. More specifically the invention relates to a method for sterilizing the inside of such a container or a package material in the form of a sheet or a web intended for a container.

BACKGROUND OF THE INVENTION

When foods are added to a container ready to be filled it is required that the container is sterilized in such a way that the likewise sterilized product under sterile conditions can be added aseptically, the container then being sealed. In order to minimize the risk of the filled product being reinfected by microorganisms the sterilization of the container and the addition of the sterilized filling material in question should take place as closely connected as possible.

Containers ready to be filled in the form of a bowl or a can are presently sterilized by means of treatment with steam, steam/condensation or hydrogen peroxide. However, containers manufactured from a soaking paper or cardboard layer rapidly lose their mechanical strength properties, and thus a container easily becomes flabby and cumbersome when it is exposed to liquid or moisture during the sterilization procedure. When chemical sterilization with hydrogen peroxide is used, for example a 3% solution, the hydrogen peroxide is sprayed on all the internal surfaces of the container, and then is allowed to act for about 20 minutes. The hydrogen peroxide is converted to water and oxygen in course of time but problems with residual amounts can remain in the same way as when other types of chemical sterilization are used.

An electromagnetic radiation can also—in dependence of dose and energy—harm microorganisms and viruses in different ways. However, the practical use of this type of sterilization is limited by the ability of the radiation to penetrate and the availability of a suitable radiation source.

The sterilizing effect of electrons has been known for a long time. An exposure to electrons is a well known sterilization method and the mechanism behind the killing is thoroughly studied. However, the ability of the electrons to penetrate a package material is relatively low but depends of course on the radiation energy. Electron guns have been developed for food containers with the purpose of sterilizing relatively thin containers from the outside, and such a sterilization method has for several years been contemplated for an additional use within the packaging industry.

Up to now however, a problem with this type of sterilization has been the large volume of the equipment since electron guns having a large capacity will occupy a space of up to 1–5 m³. Furthermore, the equipment has been too expensive to be commercially acceptable, the costs amounting to 5 millions of SEK per unit. This has led to it being impossible to manufacture commercial sterilization equipments based on electron guns.

An additional problem with the existing electron guns is that they work at such a high voltage as about 150 kV or more. Since X-rays are generated as a secondary effect when electron guns are used a shield of lead must be used to protect the personal, which shield has to be properly enclosed. It would thus be of great advantage if an equipment containing lead could be avoided when foods are produced, such as for example in a dairy.

It is thus desirable that the present problems mentioned above could be avoided concerning the sterilization of containers which are ready to be filled. There is at the same time a need for a fast sterilization method in which the sterilization step reduces the cycle time of the sterilization process.

SUMMARY OF THE INVENTION

The purpose of the invention is to provide a method of the kind mentioned above, which in a rapid, cheap and simple way permits sterilization of containers which are ready to be filled.

In order to achieve this purpose the method according to the invention has the characterizing features of claim 1.

BRIEF DESCRIPTION OF THE DRAWINGS

In order to explain the invention in more detail reference is made to the accompanying drawing in which FIG. 1 schematically shows a cross section through a container sterilized according to a preferred embodiment of the invention, and FIG. 2 schematically shows a cross section through a container sterilized according to an alternative embodiment of the invention.

BRIEF DESCRIPTION OF THE PREFERRED EMBODIMENT

The method according to the invention is made available by a cheap and small electron gun now being obtainable. Such an electron gun is described in US-A-5 414 267. This gun is constructed as a tube which is about 4 cm in diameter and about 15 cm long.

Figure 1:
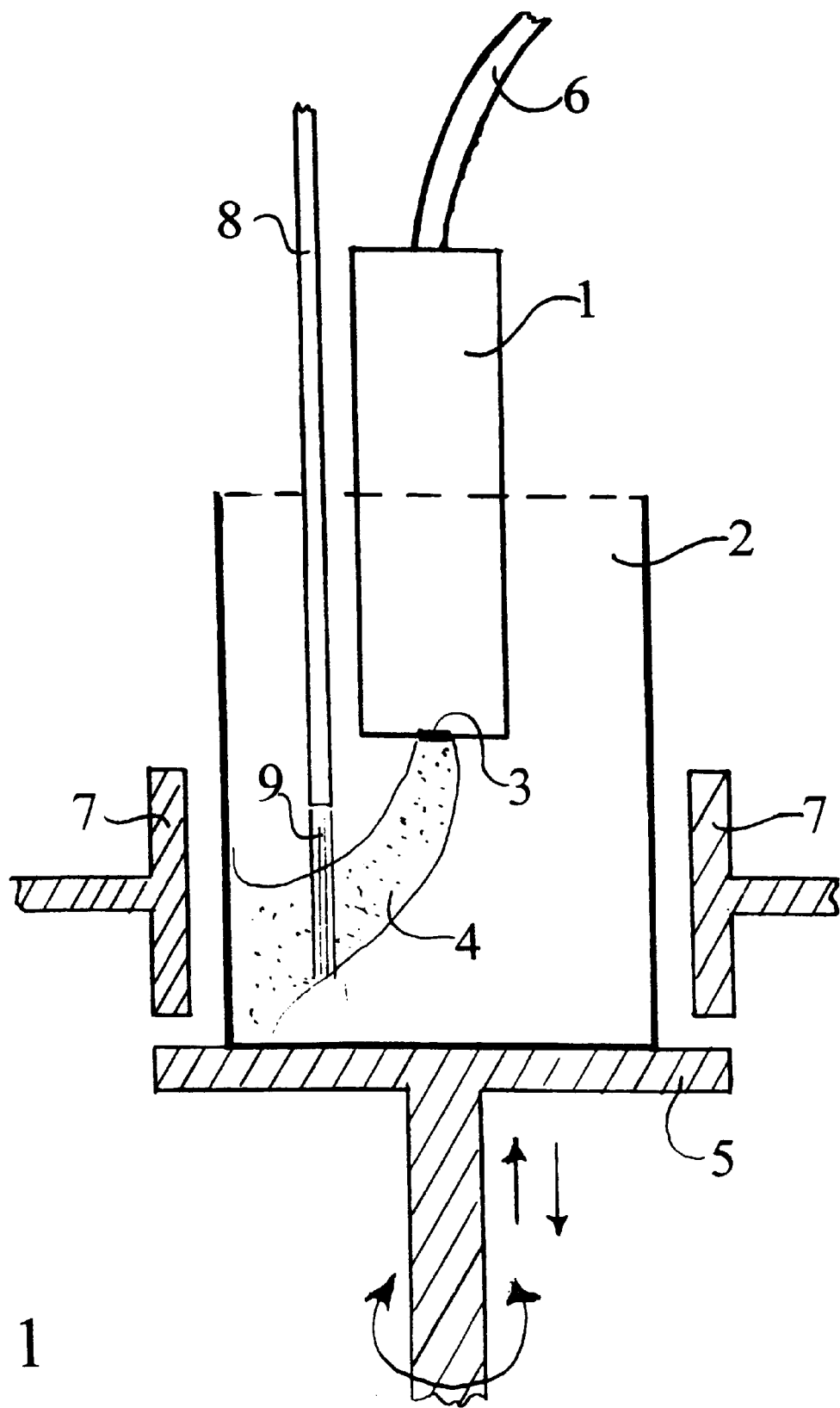

Such an electron gun 1 is schematically shown in FIG. 1 lowered into a container 2 which is to be sterilized according to the invention. A container which is ready to be filled in the form of for example a bowl, a capsule, a sleeve or a tube, and the container is preferably intended to be used for foods.

A window 3 is arranged at one end of the electron gun 1 and is at present designed as a narrow slit. An electron flow 4 leaves the electron gun through the window with the purpose of sterilization by means of radiation according to the invention. Alternatively, several windows can be arranged on the outside of the electron gun designed as a tube in order to distribute the radiation as much as possible.

The container 2 is arranged on a plate 5, preferably by means of suction, the plate 5 being rotatable as well as translatable up and down. These movements do not necessarily have to be linear, but preferably follow a specific cycle so that a uniform control of the electron flow 4 is achieved. It is also possible to change the position of the electron gun 1 in a similar way. However, this is less preferred since the gun is provided with high voltage terminals 6.

The electron gun is switched on when it is lowered into the container and is switched off when the gun is withdrawn. It is important that as uniform a dose of electrons as possible is achieved on the inside of the container so that equal amounts of energy are deposited everywhere. Preferably, the electron beam 4 is controlled by means of deflection plates 7, between which a field (e.g. a magnetic field or an electric field) is generated, a homogeneous radiation being achieved in every direction when the gun is symmetrically lowered into the container. The beam can thus be moved, for example magnetically, to any point within the container. An especially strong magnetic field is not required for the deflection of the electrons since these are low energy, and the electrons move rather slowly with said electron gun working within the interval 40–80 kV. When the plate 5 is rotated two deflection plates 7 are preferably arranged opposite each other on each side of the electron beam 4. With two additional deflection plates arranged opposite each other the electron beam can be made to sweep over the total internal surface of the container and the rotation of the plate 5 can then be excluded.

The electron beam can additionally be controlled by varying the acceleration of the electrons, a changed intensity and energy of the beam being achieved. This results in that the beam has different reaches within the individual container. Furthermore, the same equipment can be used for different types of containers.

A control of the electron beam can also be accomplished by an additional window being arranged on the outside of the electron gun in such a way that the walls of the container as well as its bottom at the same time can be exposed to electrons from the electron gun.

Furthermore, a sterilization by means of electron exposure has the advantage of the electrons penetrating the exposed material somewhat, i.e. a certain depth effect is achieved. This is an advantage since the package material used seldom has an absolutely smooth surface.

According to the invention the electron gun is thus activated and the entire gun is lowered into the container with the purpose of sterilizing its inside, the gun is then withdrawn from the container and deactivated. By this design of the sterilization step a fast sterilization method is achieved with a reduced cycle time. In comparison with sterilization with hydrogen peroxide or the like the sterilization period is considerably shorter, i.e. less than one second, and the problem with residual amounts is avoided. The short sterilization time in combination with the used load voltage of the electron gun results in considerably less energy being required for sterilization, which drastically reduces the sterilization costs.

Furthermore one or several tubes 8 can according to the invention be arranged adjacent to the electron gun 1, through which tube a gas stream 9 can be supplied to the container with the purpose of influencing the sterilization process. If for example helium is added, e.g. in the form of short jets, a range of the electrons is achieved which is about 5 times longer than that achieved without adding gas. Small portions of this gas is thus distributed to such places as corners and the like which are difficult to reach for sterilization. This results in a higher degree of sterilization by the electron beam in these places.

Instead-or at the same time-for example adding pure oxygen via another tube singlet oxygen can be generated, the sterilization effect then being drastically increased by the formation of extremely reactive peroxide radicals which have a killing effect in biological material. The sterilization effect can thus be increased by replacing the air with pure oxygen (or some other gas mixture) in the area where the electron beam strikes the surface of the container. Such free radicals are generated when gas molecules collide with electrons from the electron gun.

Figure 2:
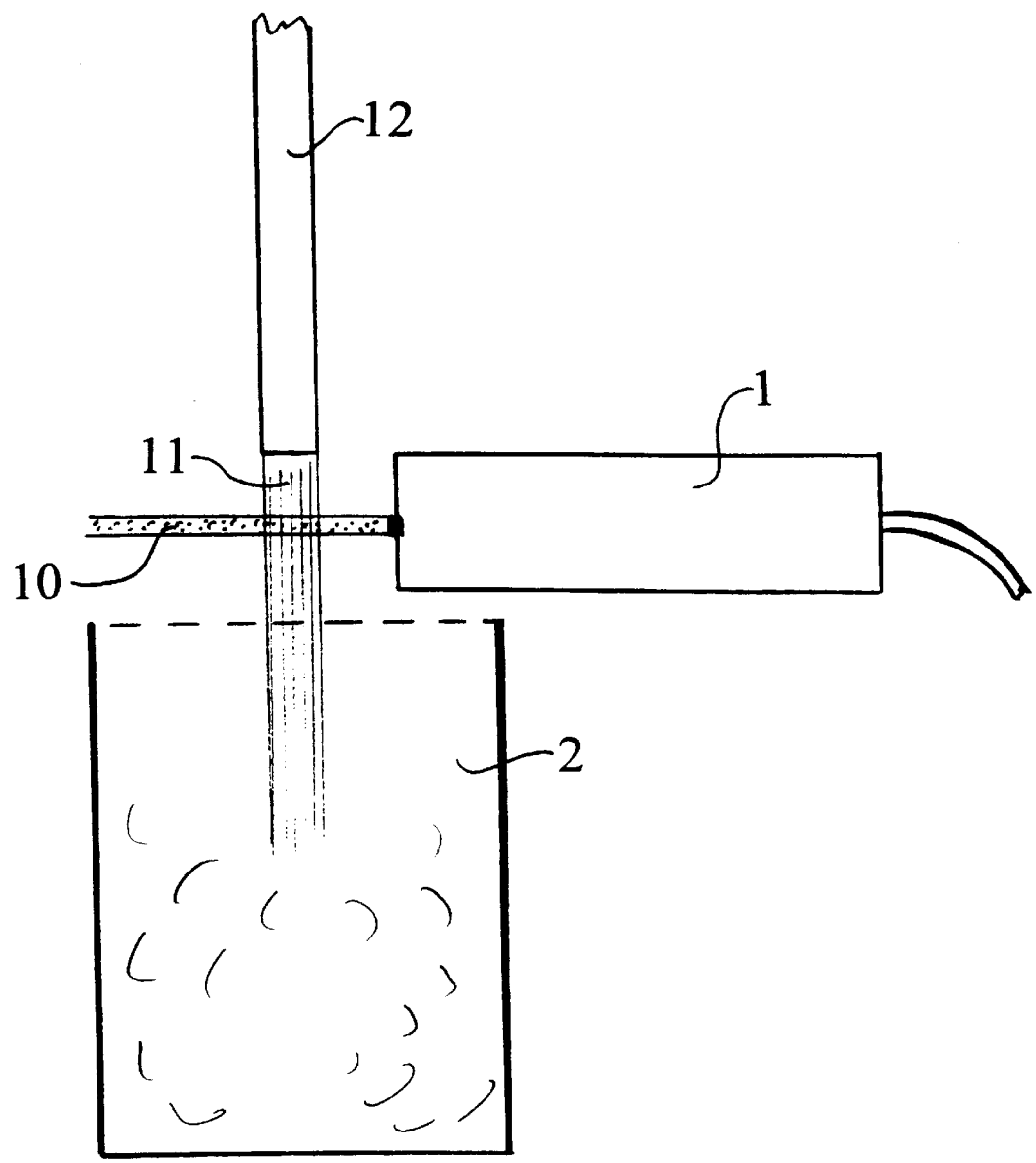

An additional sterilization effect according to the invention can be obtained by radiation, by means of an electron beam, since certain package materials when exposed to electrons give rise to off-taste problems in foods. This embodiment of the invention is shown in FIG. 2. In order to avoid a later impairment of the filling material the electron gun is arranged in such a way that an electron beam 10 is not directly aimed at the container 2. Instead, a gas stream 11 is added to the container transverse the electron beam 10, preferably perpendicular thereto, via a tube 12 which ends between the electron beam and the opening of the container. In this case the gas stream 11 consists of a gas which easily can be ionized and which preferably is oxygen.

In this embodiment the electron beam is utilized as an ion generator, i.e. the electrons are ejected from the atoms in the gas mixture used, active ions being formed. These active ions have by per se a sterilizing effect on the material. Also in this embodiment of the invention the electrons can be deflected in a magnetic field in the same way as described for electrons above.

In another embodiment of the invention the container is formed from a package material in the form of a web, the contemplated inside of which is sterilized in a corresponding way as indicated above. Several electron guns are arranged in a row above a plane packaging web and the web is preferably continuously exposed to the radiation.

One or several electron guns can also be arranged on the outside of a container. This is applicable for a plane web as well as a container which is ready to be filled.

The sterilization method according to the invention should be performed in a sterilization chamber, preferably at a pressure above the atmospheric, but a normal pressure can also be used.

An additional advantage is obtained by the radiation sterilization according to the invention. By the fact that the electrons from the electron gun all the time are slowed down by matter X-rays will be generated as a secondary effect. These X-rays have a long range and surfaces on existing equipment in the sterilization chamber will be sterilized by means of their effect. If the sterilization chamber is symmetrically designed it will be continuously exposed to the secondary radiation. Thereby an extra problem is eliminated which consists of keeping the sterilization chamber clean, and this results in that the sterilization costs being further reduced.

However, the use of a lower voltage in comparison with other electron guns, which voltage lies within the interval 40–80 kV, results in the X-rays becoming so low energy that lead protections and the like can be reduced. Stainless steel can be sufficient to protect the staff at a lower load voltage.

What is claimed is:

1. A method for sterilizing the inside of an empty container comprising:
   a) providing an empty container which is ready to be filled or a package material for a container in the form of a sheet or web;
   b) providing an electron gun;
   c) providing at least one gas stream supply tube;
   d) activating the electron gun to emit an electron beam;
   e) subjecting the inside of the container or the surface of the material to the electron beam by axially moving the gun relative to the inside or the surface; and
   f) adding a gas stream through the at least one gas supply tube to the inside of the container or the surface of the material to allow contact between the gas stream and the electron beam, wherein sterilization of the inside of the container or surface of the material is effected when the electron beam and gas stream contact each other and the inside or the surface.

2. A method for sterilizing the inside of a container, according to claim 1, wherein the gas stream (9, 11) contacting the electron beam (4–10) is added to the inside or the surface for the purpose of influencing the sterilization effect.

3. A method for sterilizing the inside of a container, according to claim 1, wherein the gas stream (9, 11) contacting the electron beam (4–10) is intermittently added to the inside or the surface.

4. A method for sterilizing the inside of a container, according to claim 1, wherein the gas stream (9, 11) consists of an easily ionized gas.

5. A method for sterilizing the inside of a container, according to claim 1, wherein the gas stream (9, 11) consists of oxygen for the purpose of achieving singlet oxygen.

6. A method for sterilizing the inside of a container, according to claim 1, wherein the gas stream (9, 11) consists of helium for the purpose of increasing the range of the electron beam (4).

7. A method for sterilizing the inside of a container, according to claim 1, wherein the gas stream (9, 11) is added to the inside or the surface substantially perpendicular to the electron beam (10).

8. A method for sterilizing the inside of a container, according to claim 1, wherein opposing deflection plates (7) are provided on each side of electron beam (4) to allow for sweeping of the electron beam over the total inside or the surface.

9. A method for sterilizing the inside of a container, according to claim 8, wherein said deflection plates (7) consist of magnets.

10. In a method of sterilizing an empty container by exposing the inside of an empty container to an electron beam comprising the steps of providing an empty container which is ready to be filled; providing an electron gun; activating the electron gun to emit an electron beam; subjecting the inside of the container to the electron beam, the improvement comprising the additional steps of: providing at least one gas stream supply tube; and adding a gas stream through the at least one gas supply tube to the inside of the container to allow contact between the gas stream and the electron beam, wherein sterilization of the inside of the container is effected when the electron beam and gas stream contact each other and the inside.

11. In a method of sterilizing as in claim 10, wherein said electron gun (1) is designed as a tube.

12. In a method of sterilizing as in claim 10, wherein the sterilization effect is achieved by causing the electron beam (4) to sweep over the entire inside of the container.

13. In a method of sterilizing as in claim 10, wherein the gas stream (11) is an easily ionized gas and the sterilization effect is achieved by causing the gas stream to be added to the inside of the container (2) substantially traversing the electron beam (10).

14. In a method of sterilizing as in claim 10, wherein the sterilization is effected over a time period of not more than one second.

15. In a method of sterilizing as in claim 10, wherein the electron gun is lowered axially into the container.

* * * * *